United States Patent
Zhang

(10) Patent No.: US 8,862,216 B2
(45) Date of Patent: Oct. 14, 2014

(54) ADAPTIVE CARDIAC DATA PATIENT FILTER SYSTEM

(71) Applicant: Hongxuan Zhang, Palatine, IL (US)

(72) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 13/760,124

(22) Filed: Feb. 6, 2013

(65) Prior Publication Data
US 2013/0245478 A1 Sep. 19, 2013

Related U.S. Application Data

(60) Provisional application No. 61/611,040, filed on Mar. 15, 2012.

(51) Int. Cl.
- *A61B 5/0452* (2006.01)
- *G06F 3/0481* (2013.01)
- *A61B 5/00* (2006.01)
- *A61B 5/0402* (2006.01)

(52) U.S. Cl.
CPC .......... *A61B 5/0402* (2013.01); *G06F 3/0481* (2013.01); *A61B 5/725* (2013.01); *A61B 5/0452* (2013.01); *A61B 5/7203* (2013.01)
USPC ........................................ 600/521; 600/509

(58) Field of Classification Search
USPC ...................................................... 600/509
See application file for complete search history.

(56) References Cited

U.S. PATENT DOCUMENTS

| | | | |
|---|---|---|---|
| 3,967,102 A | 6/1976 | McCown | |
| 4,513,254 A | 4/1985 | Harr | |
| 5,503,160 A | 4/1996 | Pering et al. | |
| 5,511,554 A | 4/1996 | Helfenbein et al. | |
| 5,929,699 A | 7/1999 | Lewicki | |
| 6,032,166 A | 2/2000 | Signell et al. | |
| 6,290,654 B1 | 9/2001 | Karakasoglu | |
| 6,405,227 B1 | 6/2002 | Prakash | |
| 6,593,802 B2 | 7/2003 | Mariani et al. | |
| 6,636,128 B2 | 10/2003 | Rauscher | |
| 6,646,498 B2 | 11/2003 | Mohieldin et al. | |
| 6,658,284 B1 | 12/2003 | Rosen et al. | |
| 6,677,814 B2 | 1/2004 | Low et al. | |
| 7,024,006 B1 | 4/2006 | Schwartz et al. | |
| 7,212,068 B2 | 5/2007 | Onody | |
| 7,627,369 B2 * | 12/2009 | Hunt ............................ 600/516 |
| 7,747,316 B2 | 6/2010 | Graupe et al. | |
| 7,952,425 B2 | 5/2011 | Zhang et al. | |
| 8,233,972 B2 | 7/2012 | Zhang | |
| 2006/0062405 A1 | 3/2006 | McKee | |

(Continued)

FOREIGN PATENT DOCUMENTS

WO WO 2010/054409 * 5/2010

*Primary Examiner* — Michael Kahelin
(74) *Attorney, Agent, or Firm* — Brennan K Bradley

(57) ABSTRACT

A system for adaptively processing patient monitoring signals comprises an input processor for acquiring a signal having amplitude representing electrical activity of a patient heart over time. A signal processor identifies different portions of the signal associated with different phases of cardiac activity by, inverting the signal to provide an inverted signal, aligning the signal and the inverted signal in amplitude during a cardiac rest portion and identifying one or more of the different portions in response to an intersection point of the signal and the inverted signal. Multiple adaptive signal filters are used to filter multiple bandwidths of corresponding different portions of the signal.

14 Claims, 11 Drawing Sheets

Patient signal reverse transformation for signal and cardiac function segmentation

(56) References Cited

U.S. PATENT DOCUMENTS

| | | |
|---|---|---|
| 2006/0153404 A1 | 7/2006 | Gardner |
| 2007/0253577 A1 | 11/2007 | Yen et al. |
| 2008/0140403 A1* | 6/2008 | Hughes et al. ............. 704/256.1 |
| 2009/0055457 A1 | 2/2009 | Miller |
| 2009/0088655 A1* | 4/2009 | Vajdic et al. .................. 600/523 |
| 2009/0121802 A1 | 5/2009 | Tsuzuki et al. |
| 2011/0113082 A1 | 5/2011 | Alimohammad et al. |
| 2011/0137646 A1 | 6/2011 | Ahgren et al. |

* cited by examiner

FIGURE 8

| Segmented signals | Filter design specification | Filter coefficients |
|---|---|---|
| Atrial functional signal | pass frequency band: 6-25Hz<br>sampling frequency: 2000 Hz<br>filter order: 2<br>filter type: Butterworth | [1.0000, 0, -1.0000<br>1.0000, -1.9406<br>0.9420] |
| Ventricular fast functional signal | pass frequency band: 15-200 Hz<br>sampling frequency: 2000 Hz<br>filter order: 2<br>filter type: Butterworth | [1.0000, 0, -1.0000<br>1.0000, -1.5162, 0.5396] |
| Ventricular slow functional signal | pass frequency band: 1.5- 8 Hz<br>sampling frequency: 2000 Hz<br>filter order: 2<br>filter type: Butterworth | [1.0000, 0, -1.0000<br>1.0000, -1.9797,<br>0.9798] |
| Late cardiac functional signal | pass frequency band: 0.3- 3Hz<br>sampling frequency: 2000 Hz<br>filter order: 2<br>filter type: Butterworth | [1.0000, 0, -1.0000<br>1.0000, -1.9915, 0.9916] |

ADAPTIVE CARDIAC DATA PATIENT FILTER SYSTEM

This is a non-provisional application of provisional application Ser. No. 61/611,040 filed Mar. 15, 2012, by H. Zhang.

FIELD OF THE INVENTION

This invention concerns a system for adaptively processing a patient monitoring signal by filtering multiple different bandwidths of corresponding multiple different portions of the signal.

BACKGROUND OF THE INVENTION

Signal filtering is crucial to yielding high quality signals, especially in medical signal acquisition where signals are in the millivolt level, such as surface electrocardiogram (ECG), intra-cardiac electrograms (ICEG) signals and invasive blood pressure signals. In clinical applications, frequency bandwidth controlled filters (such as high pass, low pass, band pass filters) are known to improve signal to noise ratio and achieve good quality patient signals for clinical diagnosis and patient status characterization. However different portions of patient signals (such as ECG, ICEG, blood pressure, SPO2 (blood oxygen saturation) and respiration signals) usually have different characteristics and different signal frequency components. However, known signal processing and filtering methods typically fail to efficiently remove unwanted noise and filter out true patient response signals since, 1. the frequency structure and signal-noise sub-components are time varying, 2. the signal and noise are dependent on characteristics of the different signal portions, such as a QRS complex and P wave in an ECG signal because these signals are created from different functional tissue and chambers and 3. the patient signal creation, patient function procedure and patient noise components are usually nonlinear and known filters are typically linear and fail to reliably and adaptively filter the noise.

Signal acquisition units need to process signals having multiple types of noise that are variable in amplitude, frequency, function and pattern, such as patient movement noise, power line electrical noise, electrical and magnetic noise from other medical instruments in hospitals, in order to resolve a clean signal from an input source. Known filtering systems have limited ability to reduce color noise and artifact interference which shares a frequency band with cardiac signals (overlap). Known filter systems are typically linear using fixed coefficients in a digital filter and lack adaptive filtering capability desirable for use in accommodating signal transitions such as a normal to arrhythmia transition, ventricular tachycardia (VT), ventricular fibrillation (VF), myocardial ischemia or infarction. Known linear signal processing systems fail to effectively reduce nonlinear and non-stationary noise and artifacts, in cardiac signals.

The noise concerned comprises patient biological noise due to respiration or patient movement, for example and due to procedures (pacing, ablation, defibrillation, electrical cutting). In addition a noise cut off frequency may shift due to treatment. Known patient signal filters are unable to efficiently remove variable noise from patient signals. Further, known fixed low or high frequency band pass filtering fails to effectively track and cancel dynamic noise and artifacts (especially, broad band noise and semi-white noise), such as voltage/current leakage noise from an electro-cautery instrument and cardiac ablation unit. A system according to invention principles addresses these deficiencies and elated problems.

SUMMARY OF THE INVENTION

An adaptive filter system analyzes and filters an electrical patient heart activity signal using signal reverse transformation, function waveform segmentation, reconstruction, signal smoothing and shaping and applies signal pattern detection to the filtered signal to identify cardiac disorders. A system for adaptively processing patient monitoring signals comprises an input processor for acquiring a signal having an amplitude representing electrical activity of a patient heart over time. A signal processor identifies different portions of the signal associated with different phases of cardiac activity by, inverting the signal to provide an inverted signal, aligning the signal and the inverted signal in amplitude during a cardiac rest portion and identifying one or more of the different portions in response to an intersection point of the signal and the inverted signal. Multiple adaptive signal filters are used to filter multiple bandwidths of corresponding different portions of the signal.

BRIEF DESCRIPTION OF THE DRAWING

FIG. 8 is a Table showing ECG waveform portions and corresponding filter frequency bandwidth and coefficients, according to invention principles.

DETAILED DESCRIPTION OF THE INVENTION

An adaptive filter system removes unwanted nonlinear and time-varying noise (including clinical environment noise, patient bio-noise) from ECG (electrocardiogram) and ICEG (intra-cardiac electrogram) signal segments and obtains improved quality patient functional response signals with high signal to noise ratio. The filter system performs patient functional analysis and filtering (including signal reverse transformation, function waveform segmentation, reconstruction, and signal smoothing and shaping) improving the quality and reliability of medical signal acquisition. The filter system is used in conjunction with a patient signal pattern and mode diagnosis function to facilitate identifying cardiac disorders, differentiating cardiac arrhythmias, characterizing pathological severity, predicting life-threatening events, and evaluating drug delivery effects. The system provides cardiac function, nonlinear multi-band, frequency controllable, adaptive filtering. In response to identification of heart function, different filters are used for different ECG signal portions and patient signals. Noise components in each portion of a patient cardiac electrical activity signal are different, so noise frequency bandwidth, noise component energy, and noise distribution differ.

Figure 1:
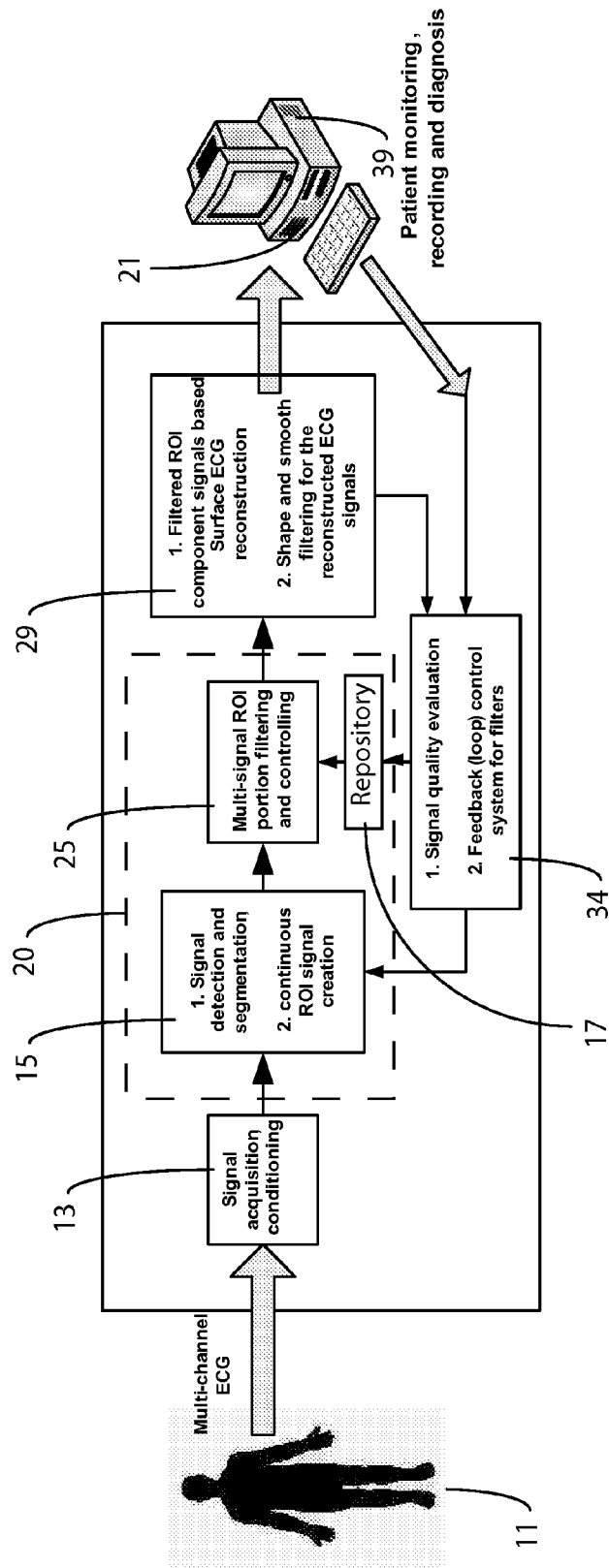
FIG. 1 shows a system for adaptively processing patient monitoring signals, according to invention principles.

FIG. 1 shows system 10 for adaptively processing patient monitoring signals using an adaptive closed loop controlled filter. A surface ECG signal having an amplitude representing electrical activity of a heart over time is acquired from patient 11 and conditioned by input processor 13 (for voltage level, lead construction variation and calibration by buffering, digitization and conditioning) based on patient context and a clinical application being performed. Signal processor 20 includes repository 17, segmentation and processing unit 15 and adaptive filters 25. Segmentation and processing unit 15 identifies different portions of the conditioned signal from unit 13 associated with different phases of cardiac activity by, inverting the signal to provide an inverted signal, aligning the signal and the inverted signal in amplitude during a cardiac rest portion and identifying one or more of the different portions in response to an intersection point of the signal and the inverted signal. Adaptive signal filters 25 filter multiple bandwidths of corresponding different portions of the conditioned, segmented signal. Different kinds of signal filters are applied to corresponding signal segments and in one embodiment a nonlinear filter is used with automatic feedback loop control of filter parameters and coefficients in different signal portions.

Following segmentation and filtering, the surface ECG signal is reconstructed into multiple continuous component signals associated with signal portions, such as atrial functional signals, ventricular signals. Filtered component signals are reconstructed by signal reconstruction processor 29 into a surface ECG signal and a shape and smoothing filter in unit 29 is used to smooth out and remove nonlinear changes in the reconstructed signal. The reconstructed signal is stored in repository 17 and provided to patient monitor 39 for display and storage. Display processor 21 generates data representing a single display image including a window area enabling a user to individually view filter attenuation characteristics within the predetermined frequency bandwidth, of the multiple adaptive filters. Feedback control module 34 controls signal segmentation and filtering in unit 20 in response to data identifying a clinical application or procedure being performed and signal functionality, such as the number of segments of the signal to be used and a quality indicator such as a signal to noise ratio.

In patient monitoring, high quality signals (with low noise) are desired for proper diagnosis and medical treatment decision making. However, patient millivolt (mV) or microvolt (uV) range signals are easily distorted and affected by noise, such as electrical emission noise (environmental noise), patient movement and respiration (bio-artifact) noise. System 10 provides nonlinear patient signal denoising and artifact removal for cardiac electrophysiological activities (ECG signals), for example.

Figure 2:
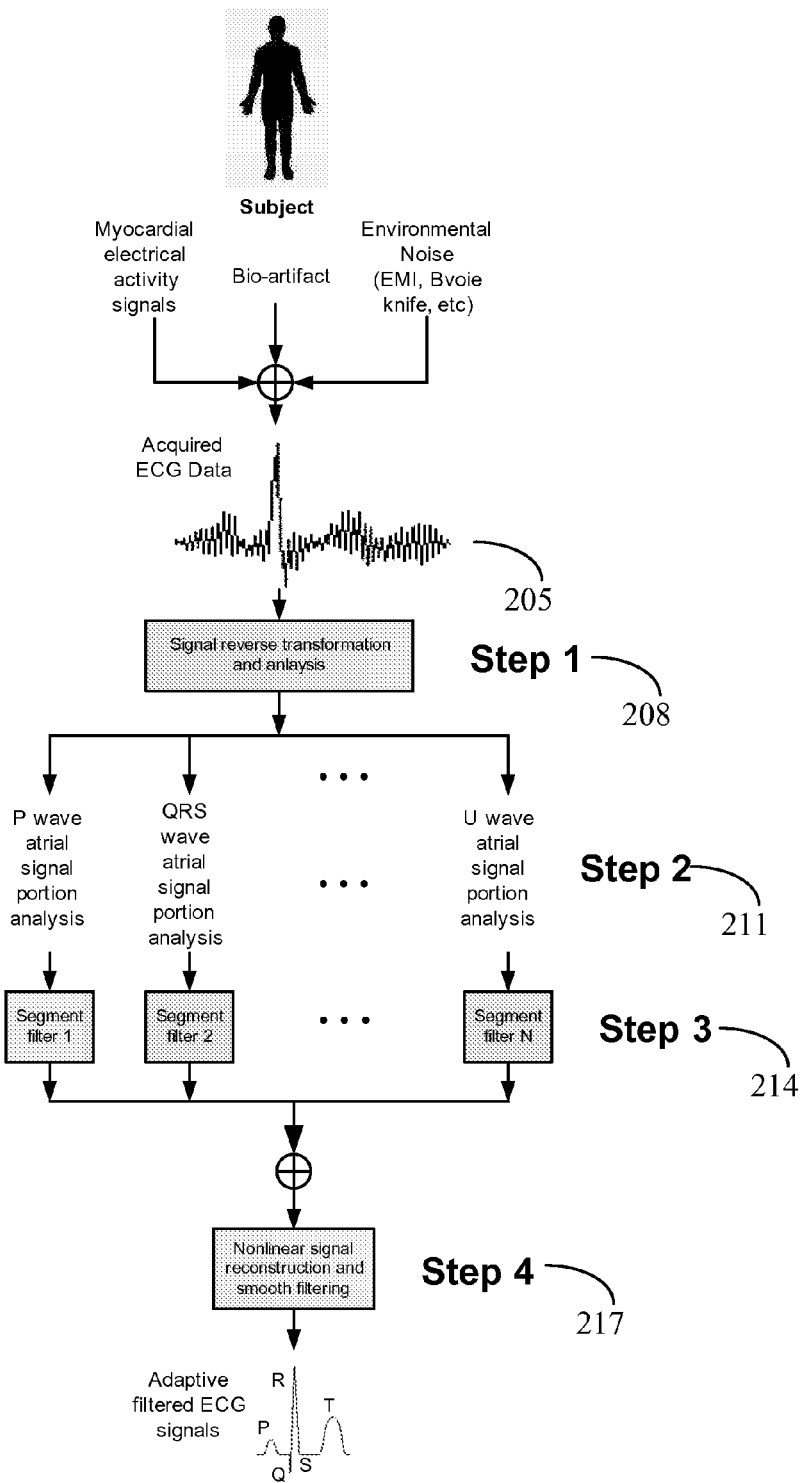
FIG. 2 shows a method for providing and reconstructing filtered segmented signal components to provide an adaptive filtered patient signal with improved signal to noise ratio, according to invention principles.

FIG. 2 shows a method for providing and reconstructing filtered segmented signal components to provide an adaptive filtered patient signal with improved signal to noise ratio. In the figure, an acquired patient signal (Surface ECG signal 205) comprises a combination of multiple components including patient electrophysiological activity of a tissue area, patient bio-noise, treatment (drug delivery, pacing, ablation) and clinical environment noise. The system in Step 1 (208) and Step 2 (211) performs a reverse transform analysis involving patient signal segmentation to extract different signal component portions from an acquired patient signal including, a P wave (atrial electrophysiological response), QRS wave (ventricular depolarization electrophysiological response), T wave (ventricular repolarization electrophysiological response) and U wave portions. System 10 (FIG. 1) in Step 3 (214) filters each segmented signal portion using an individual specific filter for each corresponding signal portion. System 10 in Step 4 (217) combines filtered segmented signal components and nonlinearly reconstructs a patient signal, which is shape filtered for denoising and artifact rejection to provide an adaptive filtered patient signal with improved signal to noise ratio.

In order to extract cardiac function information from a signal portion, a signal reverse transformation is used. Following high pass filtering, a zero line (corresponding to absence of electrophysiological activity) of a patient signal (approximately zero voltage) is used to segment a cardiac signal waveform to identify portions associated with atrial chamber activity and depolarization. However the zero line and zero voltage are easily distorted by noise from patient movement, delay and oscillation within an acquisition circuit, environmental noise and treatment noise, which impedes accurate detection of a signal portion and decreases signal analysis reliability. In one embodiment instead of using waveform peak detection the system provides a reverse transformation to more adaptively and reliably segment and extract different signal portions.

Figure 3:
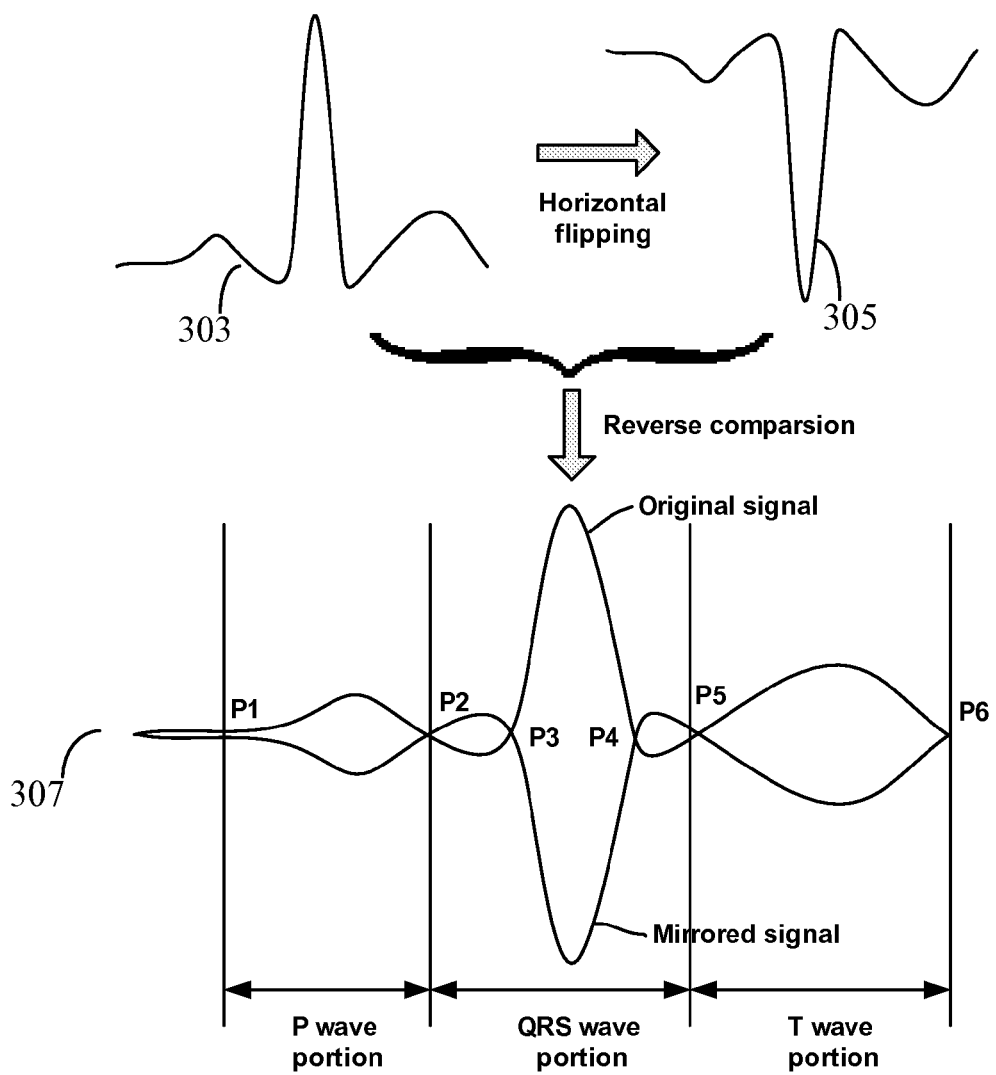
FIGS. 3 and 4 show a reverse transformation procedure for signal segmentation, according to invention principles.
Figure 4:
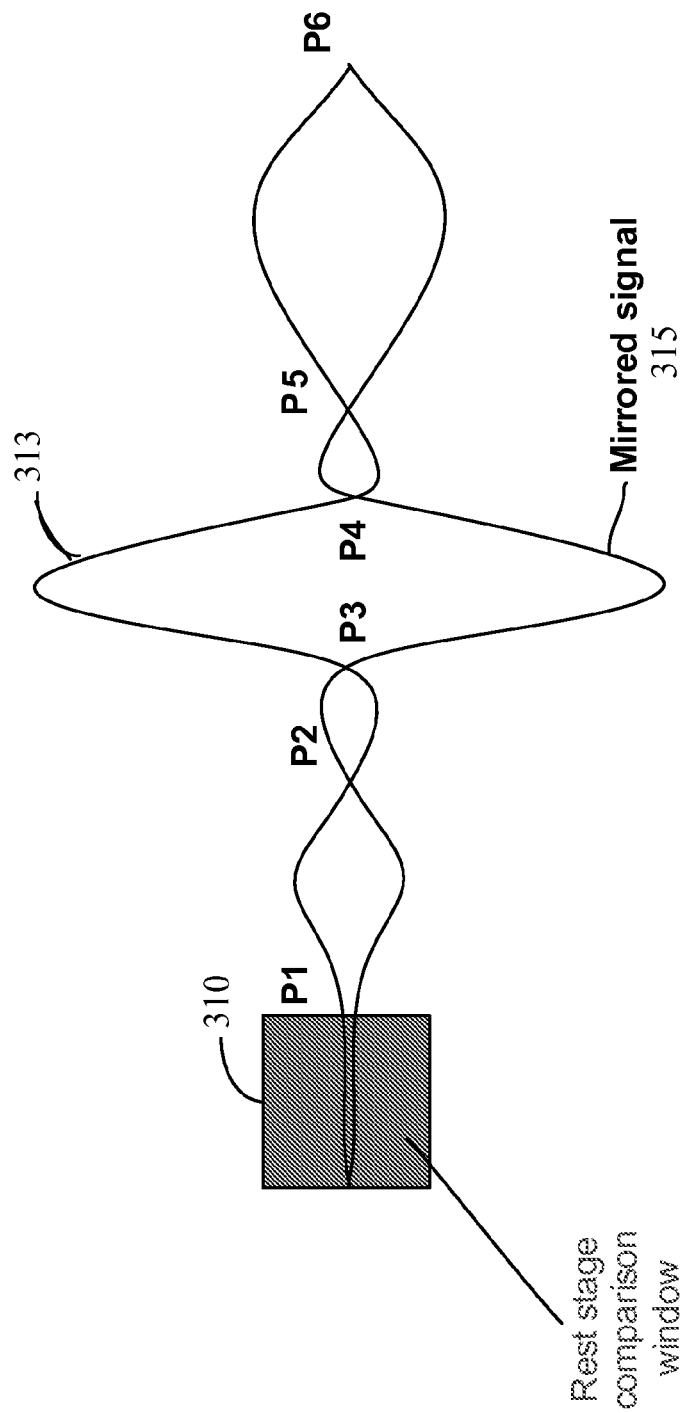

FIGS. 3 and 4 show a reverse transformation procedure for signal segmentation. The reverse transformation flips an original signal 303 horizontally to provide reversed signal 305 and compares 307 the flipped signal with the original signal waveform as a mirror image. Instead of using a zero voltage line to detect the zero crossing point, the signal reverse transformation uses the mirrored signal waveform to find common points between the two mirrored patient signals. For example in a surface ECG signal, P1, P2, P3, P4, P5, P6 are common points. Based on these common points, a cardiac cycle signal is segmented by function. A cardiac signal is segmented into portions: P1-P2 which is a P wave portion representing atrial activity; P2-P5 is a QRS complex portion showing ventricular depolarization; P5-P6 is a T wave portion showing ventricular repolarization, for example. Different kinds of patient signal may be segmented in this manner, such as SPO2 waveforms, blood pressure signals, respiration signals and patient temperature signals. The system automatically adaptively selects signal portions to segment in response to data indicating a clinical procedure being performed, and may also include P2-P3 as a Q wave portion and P3-P4 for an R wave portion, for example.

In order to perform common point detection, system 10 employs rules including, a P1 point is a last crossing point before a P wave since there may be multiple P1 points in a cardiac rest period and P2 to P6 are the 2nd to $6^{th}$ crossing waveform common points. System 10 filters out noise, such as 50-60 Hz and high frequency noise, using a notch filter and high pass filter (such as a filter with a 200 Hz cut off frequency). Bio-noise, such as patient movement induced noise, typically does not contaminate crossing point detection. In identifying segments using flipped and non-flipped signals, a variable DC offset is added to the flipped signal, for example, and the signals moved relatively to minimize an error determined in a signal rest phase when there is minimal heart activity. A comparison window for the rest stage of a single cardiac cycle is defined and the merged signals compared in the defined window and the DC offset is changed until, $$|\Sigma(|signal\_1(i)|-|signal\_2(i)|)| \leq \alpha\% \cdot \Sigma|signal\_1(i)|,$$

In which signal 313 (FIG. 4) and signal 315 stand for the original signal and flipped signal, i shows the time series of data samples in rest window 310. System 10 (or a user) may control the accuracy of the alignment and the reverse transform procedure, e.g., 0.1% ($\alpha$ %) for high accurate merging and reverse comparison. The procedure is performed using an FPGA (Field Programmable Gate Array) or DSP (Digital Signal Processor) including a microcontroller, for example.

In one embodiment, the system detects P wave, Q wave, R wave, T wave, S wave and U wave segments of a received signal by detecting peaks within the received data using a known peak detector and by segmenting a signal represented by the received data into windows where the waves are expected and by identifying the peaks within the windows. The start point of a wave, for example, is identified by different methods. In one method a wave start point comprises where the flipped and non-flipped signals intersect (cross) or alternatively cross a baseline of the merged signals (in a predetermined wave window, for example). Alternatively, a wave start point may comprise a peak or valley of signal. In one embodiment, a baseline of the signal is derived from a zero line of the mirrored signals as previously described. The signal processor includes a timing detector for determining time duration between the signal peaks and valleys. The time detector uses a clock counter for counting a clock between the peak and valley points and the counting is initiated and terminated in response to the detected peak and valley characteristics.

Figure 5:
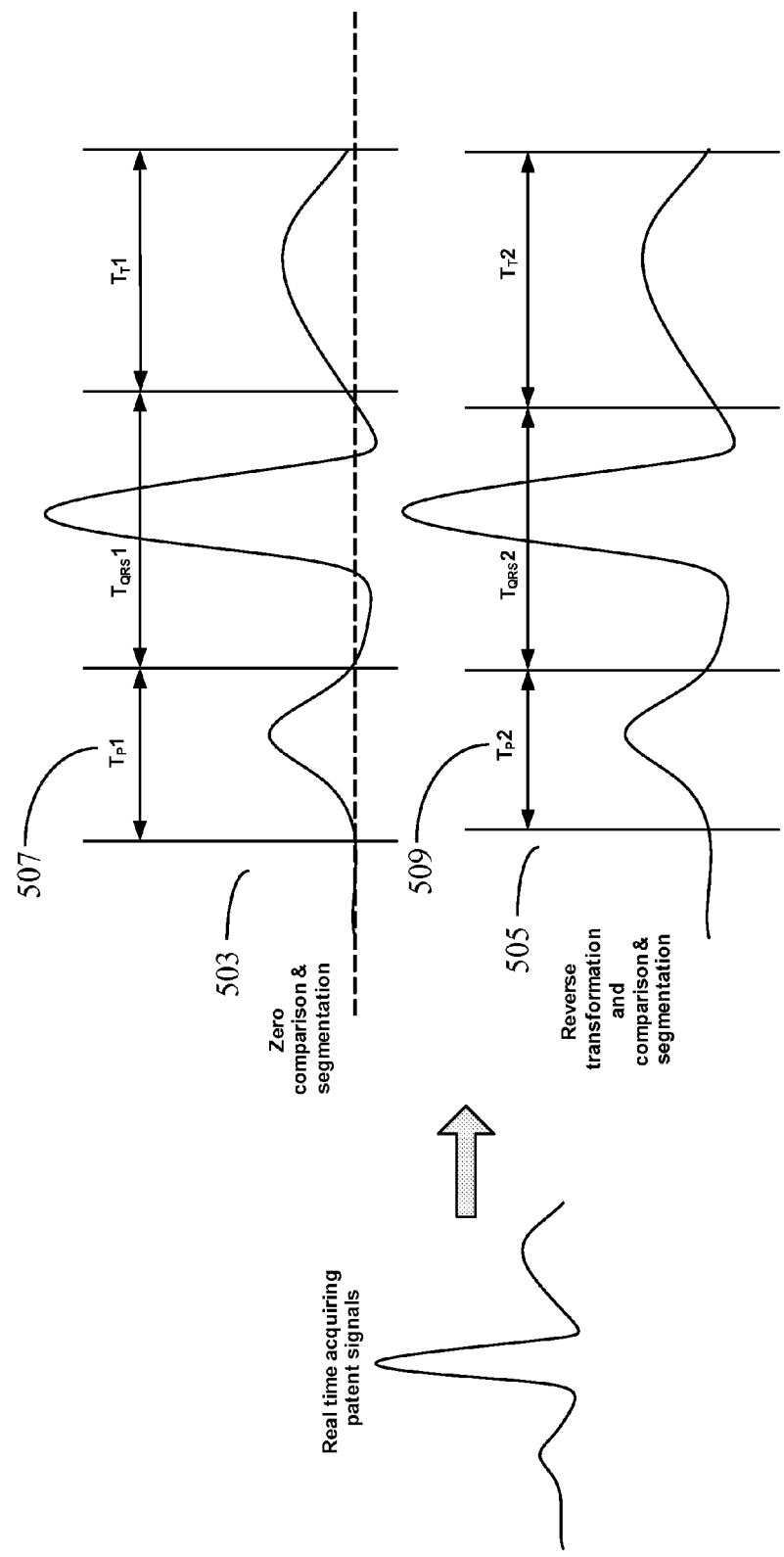
FIG. 5 shows patient signal segmentation comparison using different methods for signal extraction and segmentation, according to invention principles.

FIG. 5 shows patient signal segmentation comparison using different methods for signal extraction and segmentation. In a first method 503, signal segmentation is performed using zero-voltage-crossing and in a second method 505 signal segmentation is performed using advantageous reverse signal transformation. For example, TP1 507 and TP2 509 show P wave (atrial electrophysiological activity) sections based on zero voltage and reverse transformation, respectively. TP1 is bigger than TP2 since time duration measurement variation occurs due to zero voltage line shift and due to noise level, for example. If there is no noise or a dynamic offset voltage change due to treatment (such as ablation) and patient bio-noise (such as cough or respiration), the two methods result in similar signal segmentation. However if there is noise or introduction of a dynamic offset voltage, the zero voltage line crossing method may result in zero crossing point detection variation. In the presence of noise, the reverse transformation segmentation advantageously provides improved stability, reliability and accuracy of detection of the cardiac function transitions.

Figure 6:
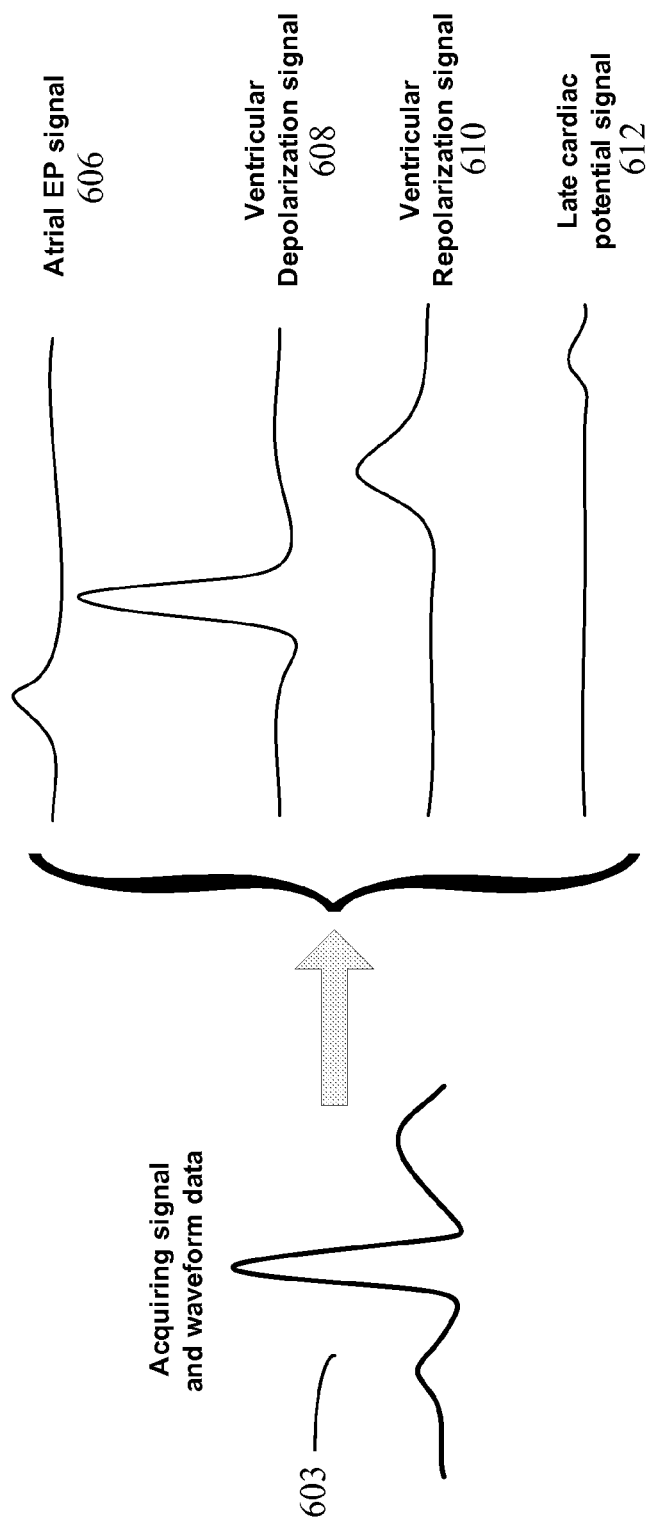
FIG. 6 shows decomposing and segmentation of an original surface ECG signal into different cardiac signal portions and tissue electrophysiological activities, according to invention principles.

FIG. 6 shows decomposing and segmentation of an original surface ECG signal into different cardiac signal portions and tissue electrophysiological activities. An ECG signal 603 is segmented and decomposed into different continuous signal components including an, Atrial action potential signal 606, ventricular depolarization potential signal 608, ventricular repolarization potential signal 610 and late cardiac potential signal 612. In this way, each patient signal is converted into different sub-signals. In one embodiment, system 10 adaptively selects between different segmentation methods in response to data indicating a clinical procedure being performed. The different segmentation methods may include PR and RS portion segmentation and applying different kinds of filtering setup and coefficients, for example. Based on the signal segmentation and separation, the relationship between an original patient signal and the derived patient function portion continuous signals is represented by, Patient signal=Atrial EP signals⊕Ventricular Depolarization signal⊕Ventricular Repolarization signal⊕Late cardiac potential signals The segmentation facilitates selection and use of coefficients based filters for filtering component signals. Between individual signal component portions, a zero (low frequency) signal baseline is used to connect component portions together. Hence, in this way, nonlinear filters efficiently reduce noise from component signals.

System 10 segments a patient signal efficiently based on patient (or organ) function. Segmentation may be performed for an SPO2 signal based on hemodynamic characteristics (such as invasive and non-invasive blood pressure signal characteristics) and in response to ECG signals or intra-cardiac electrophysiological signals. An individual portion is filtered using a corresponding filter configuration comprising different kinds of filter, having particular bandwidth, amplitude and filter order. reducing signal loss by avoiding use of a generic filter for different signal portions. Additionally, for a particular filter configuration, the coefficients (including digital filter and analogue filter coefficients) may be varied dynamically during filtering in response to patient heart rhythm, status and treatment. Coefficients may be adaptively and automatically updated and controlled by the system (or a user). Furthermore filters may be linear or nonlinear filters and the coefficients in the filters may be time varying and nonlinear.

Figure 7:
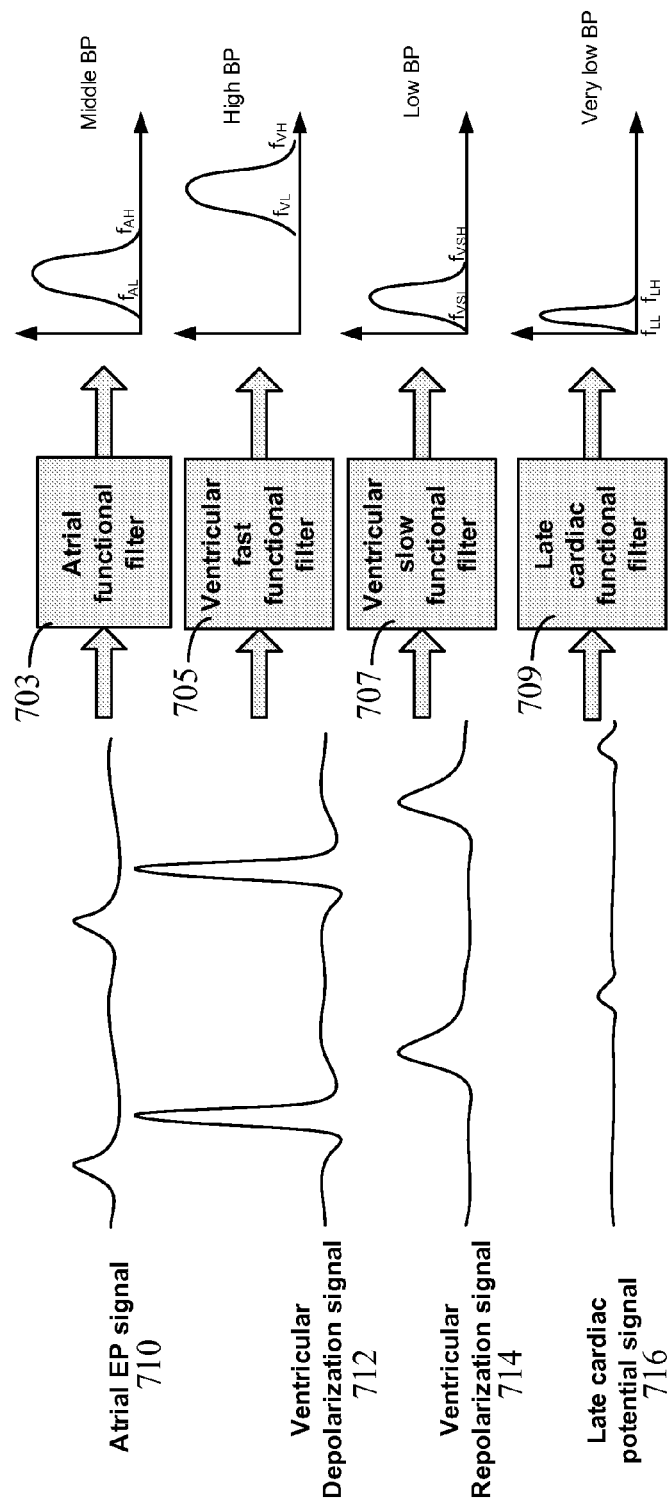
FIG. 7 shows a filter used for different segmented portions of a cardiac ECG signal, according to invention principles.

FIG. 7 shows a filter used for different segmented portions of a cardiac ECG signal. Different kinds of filter are used for noise removal of a segment of a surface ECG signal waveform including, a Middle frequency (6-25 Hz) bandwidth band pass filter 703, a High frequency (15-200 Hz) bandwidth band pass filter 705, a Low frequency (1.5-8 Hz) bandwidth band pass filter 707 and a Very low frequency (0.3-3 Hz) bandwidth band pass filter 709. A filter frequency bandwidth is selected in response to signal type, patient status and treatment. The filter is a linear filter, for example, and coefficients in these filters are adaptively updated in patient signal monitoring, recording, and diagnosis. Cardiac functional signal portions 710, 712, 714 and 716 are filtered using corresponding specific filters 703, 705, 707 and 709. For example, middle frequency band pass filter 703 filters atrial functional signals 710 and high frequency band pass filter 705 filters ventricular depolarization functional signals 712. The order, coefficients and frequency band of the filters may be dynamically varied and time varying in response to patient status, noise level, patient treatment and drug delivery. Filter factors are updated adaptively by the system.

FIG. 8 is a Table showing ECG waveform portions (column 803) and corresponding filter type and frequency bandwidth (column 805) and coefficients (column 807). Linear filters are used in one embodiment, such as FIR and IIR filters. A digital filter is characterized by its transfer function, or its difference equation. Mathematical analysis of the transfer function describes how it will respond to an input. A filter is determined by specifications appropriate to the problem (for example, a second-order low band pass filter with the specific cut-off frequencies), with a transfer function which meets the specifications. Digital filters typically comprise infinite impulse response (IIR) and finite impulse response (FIR) filters. A recursive filter with both inputs (Numerator) and outputs (Denominator) typically lead to an IIR infinite impulse response behavior, but if the denominator is made equal to unity i.e. no feedback, an FIR or finite impulse response filter is produced. The transfer function for a linear, time-invariant, digital filter may be expressed as a transfer function in the Z-domain; it has the following form, $$H(z) = \frac{B(z)}{A(z)} = \frac{b_0 + b_1 z^{-1} + b_2 z^{-2} + \ldots + b_N z^{-N}}{a_0 + a_1 z^{-1} + a_2 z^{-2} + \ldots + a_M z^{-M}}$$

In which, the order of the filter is the greater number of N or M. In this way, the FIR or IIR filter is represented by a coefficient matrix and vector, such as IIR $[b_0, b_1, \ldots, b_N, a_0, a_1, \ldots, a_N]$. The coefficient elements and vectors are generated by controlling the filter factors in the specification. These factors are, (a) if it is an IIR, pass frequency band, sampling frequency, filter order and filter type, (b) if it is an FIR filter, pass frequency band, stop band ripple, pass band ripple, transition width and sampling frequency.

An IIR filter of different order and type may be used in response to patient signal characteristics. High order filters may have good ripple suppression but longer calculation time. A filter may be a band pass filter, high pass filter or low pass filter in response to control of a frequency band. Further, in analysis of the same or different patient signal, coefficients of each sub component filter may be time varying and system 10 adaptively and automatically updates the coefficients based on patient status and treatments. In one embodiment a nonlinear filter is used with automatic feedback loop control of filter parameters and coefficients in different signal portions.

In response to signal component filtering, patient signal sub-components are added together to reconstruct the original signal but with improved signal to noise ratio. The signals reconstruction is achieved using the following function where coefficients may be used compensate for amplitude loss in sub-component filtering, $$\begin{aligned}\text{Patient signal} &= \sum_{i \in \text{segmented ROI component number}} \alpha_i \cdot \text{sub-component signals}_i \\ &= \alpha_1 \cdot \text{Atrial } EP \text{ signals} \oplus \alpha_2 \cdot \\ &\quad \text{Ventricular Depolariation signal} \oplus \alpha_3 \cdot \\ &\quad \text{Ventricular Repolarization signal} \oplus \alpha_4 \cdot \\ &\quad \text{Late cardiac potential signals}\end{aligned}$$

In which, $\alpha_i$ is a compensation coefficient for different sub-component signals. Usually compensation coefficient $\alpha_i$ is 1 but some filters may unintentionally decrease signal amplitude and $\alpha_i$ may vary. Hence an adaptive compensation coefficient may be used. There may be jitter (such as relatively high frequency noise) during multiple-component reconstruction. Hence a shape and smoothing filter such as a low pass polynomial filter having a cut off frequency of 100 Hz or 75 Hz is used to remove jitter noise, for example.

Figure 9:
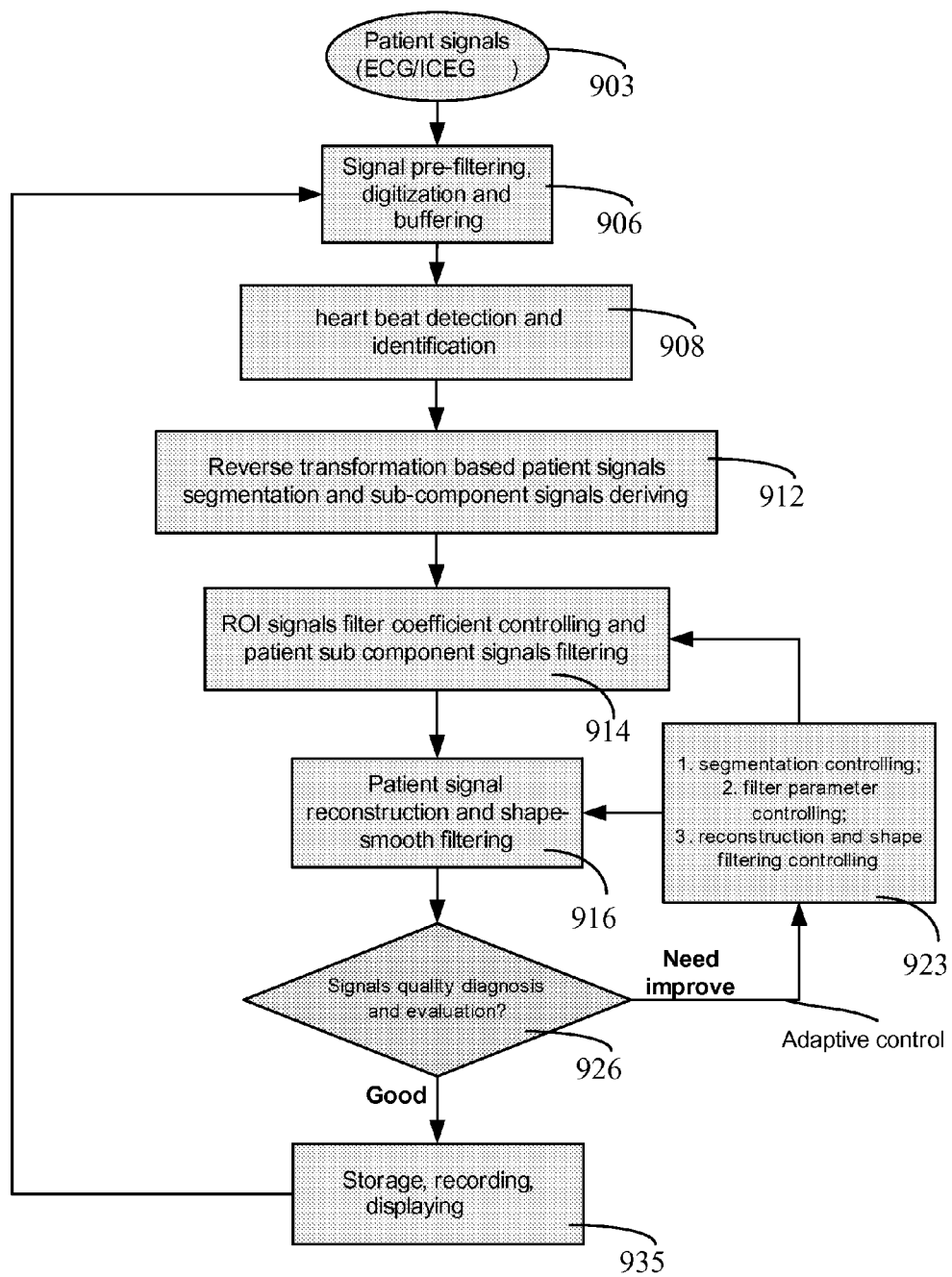
FIG. 9 shows a flowchart of a process used by a system for adaptively processing patient monitoring signals with improved signal to noise ratio, according to invention principles.

FIG. 9 shows a flowchart of a process used by system 10 (FIG. 1) for adaptively processing and filtering patient signal sub-components with improved signal to noise ratio. In step 903, input processor 13 acquires an ECG or an ICEG signal having an amplitude representing electrical activity of a patient heart over time. Processor 13 in step 906 buffers, digitizes and uses a filter adaptively selected in response to data indicating clinical application to remove patient movement and respiratory artifacts as well as power line noise (using a 50-60 Hz notch filter), for example. In step 908, signal processor 20 detects a cardiac cycle and in step 912 performs a reverse transformation analysis including signal separation and segmentation of at least one complete heart cycle. Processor 20 identifies different portions of the signal associated with different phases of cardiac activity by, inverting the signal to provide an inverted signal, aligning the signal and the inverted signal in amplitude during a cardiac rest portion and identifying one or more of the different portions (sub-components) in response to an intersection point of the signal and the inverted signal. An ECG signal is segmented into predetermined sections including Q, R, S, T, U wave segments within a heart cycle.

Processor 20 in step 914 employs multiple adaptive signal filters for filtering multiple bandwidths of corresponding different portions of the signal using automatic and adaptive filter coefficient control and by continuous filtering of sub-components. Processor 20 also adaptively configures the filters in response to signal quality, e.g., detected SNR (signal to noise ratio). In step 916, reconstruction processor 29 performs patient signal reconstruction from the filtered sub-component and segmented signals and employs a shape and smoothing filter to improve a reconstructed patient signal. Processor 29 in step 926 determines quality of the filtered reconstructed signal by measurement of SNR and if the quality exceeds a predetermined threshold, in step 935 stores the filtered reconstructed signal and patient data presented on patient monitor 39 in repository 17 and iteratively repeats the process from step 906. If the quality is below a predetermined threshold, processor 29 in step 923 adaptively adjusts sub-component and reconstruction filter coefficients and segmentation.

Figure 10:
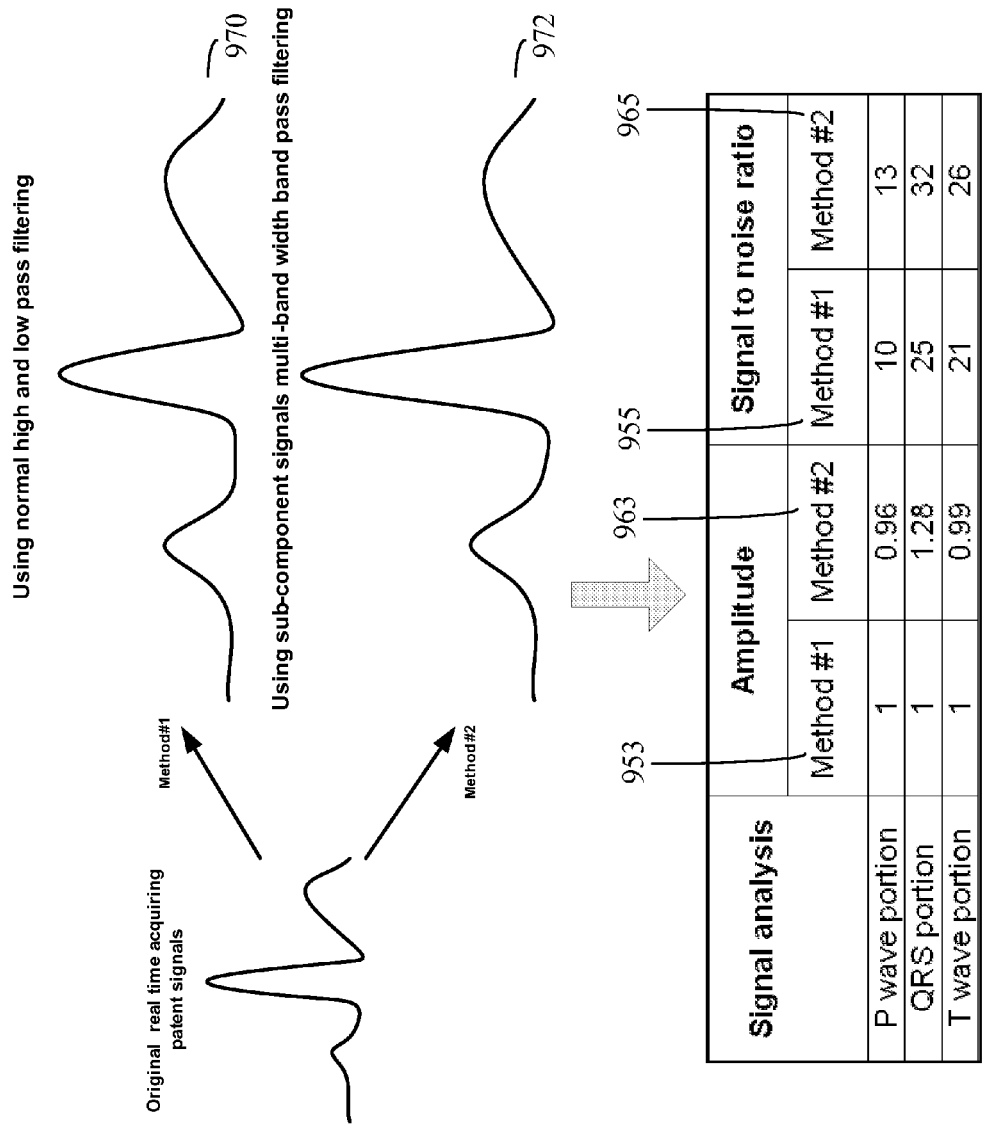
FIG. 10 shows comparison of a known filter method and a sub-component filter, according to invention principles.

FIG. 10 shows comparison of a known filter method 1 and a sub-component filter method 2 of system 10 (FIG. 1). Known normal low pass filter method 1 with bandwidth 0.05-200 Hz provides signal 970 and system 10 reverse transformation and segmentation filter method 2 with adaptively controlled frequency bandwidth provides signal 972. Method 1 employs a typical known filter (including notch filter, 50-60 Hz; high pass filter, 1-∞ Hz; low pass filter, 0-75 Hz). Method 2 employs system 10 segmented multi-sub-component filters where the patient ECG signal is segmented into a P wave portion, QRS portion, and T wave portion. Each portion is filtered using a different band pass filter, 0.5-25 Hz for P wave, 5-150 Hz for QRS complex, and 1-10 Hz for a T wave portion. Filtered signal quality (signal to noise ratio) of Method 2 (column 965) is improved compared to signal quality (signal to noise ratio) of Method 1 (column 955). Further, as shown in columns 953, 963, 955, 965 comparing method 2 with method 1, P wave portion signal amplitude has decreased 4%, but signal to noise ratio has increased 30%; QRS complex signal amplitude has increased 28% and signal to noise ratio has increased 28%; T wave portion signal amplitude has decreased 1% but signal to noise ratio has increased 24%. The waveform morphology shows the filtered ECG signal waveforms from both methods look smooth and clean. However, the QRS complex portion from method 1 has drastically decreased compared with method 2. Hence based on overall signal morphology and numerical calculation, Method 2 more effectively filters the noise from the P wave and T wave portions, and preserves more of the signal in the QRS complex portion.

Figure 11:
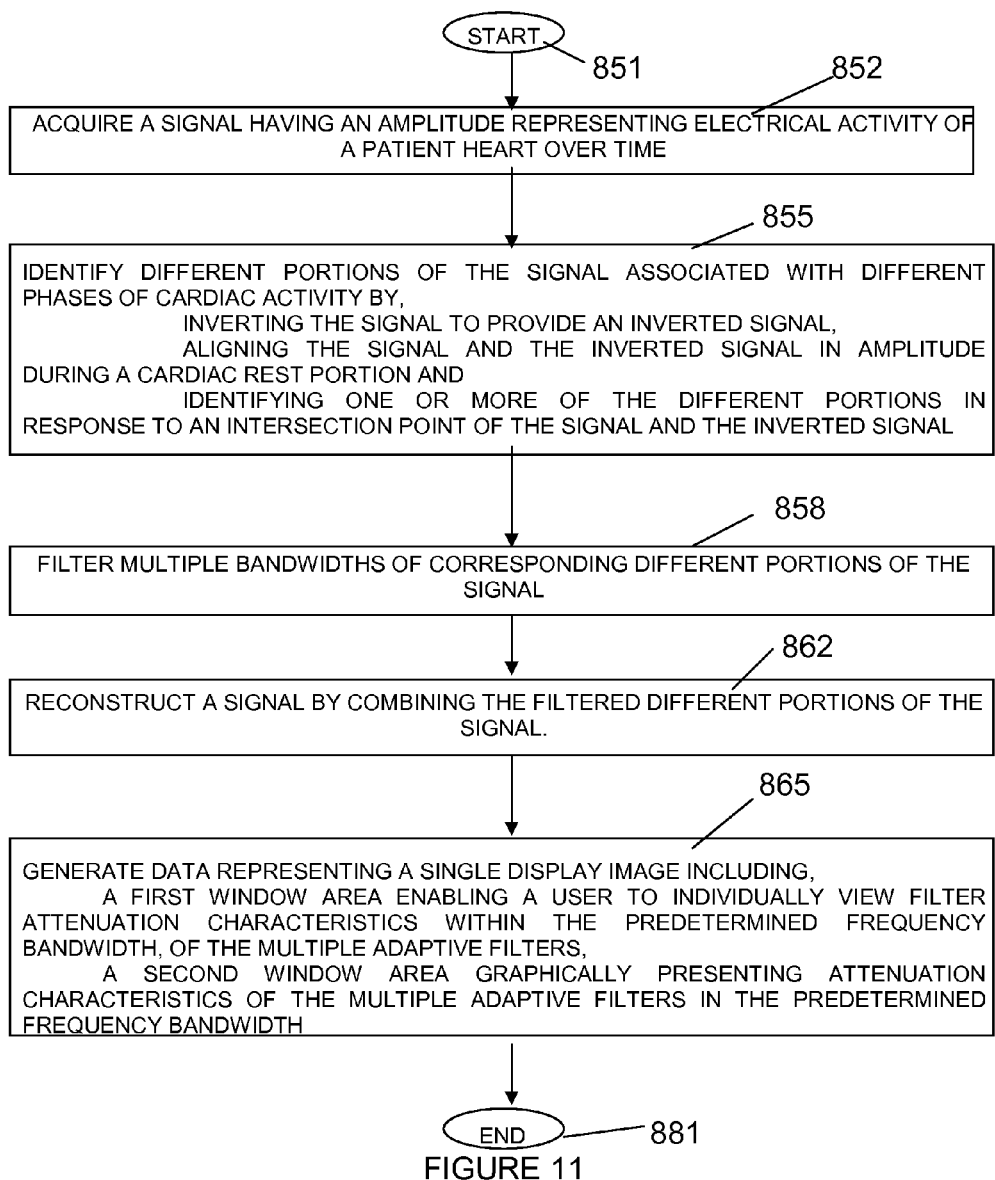
FIG. 11 shows a flowchart of a process used by a system for adaptively processing patient monitoring signals, according to invention principles.

FIG. 11 shows a flowchart of a process used by system 10 (FIG. 1) for adaptively processing patient monitoring signals. In step 852 following the start at step 851, input processor 13 acquires a signal having an amplitude representing electrical activity of a patient heart over time. Signal processor 20 in step 855 identifies different portions of the signal associated with different phases of cardiac activity by, inverting the signal to provide an inverted signal, aligning the signal and the inverted signal in amplitude during a cardiac rest portion and identifying one or more of the different portions in response to an intersection point of the signal and the inverted signal. Signal processor 20 identifies the rest phase as comprising between a U wave and a P wave and aligns the signal and the inverted signal in amplitude by at least one of, (a) applying a DC offset to a signal and (b) voltage clamping a signal. The different portions comprise at least two of P wave, QRS wave, T wave, S wave and U wave portions of the signal. In step 858, multiple adaptive signal filters in processor 20 filter multiple bandwidths of corresponding different portions of the signal. The multiple adaptive signal filters are at least one of, (a) digital and (b) analog, filters that individually have a filtering bandwidth and filtering characteristic programmable in response to received programming data derived in response to data indicating type of medical procedure being performed. The programmable filtering characteristic of the multiple adaptive signal filters determine whether the filter is at least one of, (a) a low pass filter, (b) a high pass filter and (c) a bandpass filter.

Reconstruction processor 29 in step 862 reconstructs a signal by combining the filtered different portions of the signal. Signal reconstruction processor 29 reconstructs a signal by combining the filtered different portions of the signal and in one embodiment, provides a reconstructed signal by summing the filtered different portions of the signal. In another embodiment, processor 29 provides the reconstructed signal by performing a weighted summation of the filtered different portions of the signal. In step 865, display processor 21 generates data representing a single display image including, a first window area enabling a user to individually view filter attenuation characteristics within the predetermined frequency bandwidth, of the multiple adaptive filters and a second window area graphically presenting attenuation characteristics of the multiple adaptive filters in the predetermined frequency bandwidth. The process of FIG. 11 terminates at step 881.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An adaptive filter system removes unwanted non-linear and time-varying noise (including clinical environment noise, patient bio-noise) from ECG (electrocardiogram) and ICEG (intra-cardiac electrogram) signal segments and obtains improved quality patient functional response signals with high signal to noise ratio. An adaptive filter system filters different (e.g. successive) ECG signal portions and other patient signal portions with corresponding different filter functions to accommodate differences in noise frequency bandwidth, noise component energy, and noise distribution between the signal portions. Further, the processes and applications may, in alternative embodiments, be located on one or more (e.g., distributed) processing devices on a network linking the units FIG. 1. Any of the functions and steps provided in FIGS. 1-11 may be implemented in hardware, software or a combination of both. No claim element herein is to be construed under the provisions of 35 U.S.C. 112, sixth paragraph, unless the element is expressly recited using the phrase "means for."

The invention claimed is:

1. A system for adaptively processing patient monitoring signals, comprising:
   an input processor configured to acquire a signal having an amplitude representing electrical activity of a patient heart over time;
   a signal processor configured to identify different portions of said signal, where each of the different portions is associated with a respective phase of cardiac activity, by:
   inverting said signal to provide an inverted signal;
   aligning said signal and said inverted signal based on their respective amplitudes during a cardiac rest portion; and
   identifying one or more of the different portions of said signal based on one or more intersections point of said aligned signal and inverted signal; and
   a plurality of adaptive signal filters, each of the plurality of adaptive signal filters configured to filter a respective plurality of bandwidths of a respective one of the different portions of said signal.

2. A system according to claim 1, wherein said different portions comprise at least two of P wave, QRS wave and T wave portions of said signal.

3. A system according to claim 2, wherein said different portions comprise at least one of, S wave and U wave portions of said signal.

4. A system according to claim 1, wherein
   said signal processor,
   identifies said cardiac rest portion as comprising between a U wave and a P wave and
   aligns said signal and said inverted signal based on their respective amplitudes by at least one of, (a) applying a DC offset to a signal and (b) voltage clamping a signal.

5. A system according to claim 1, wherein said plurality of adaptive signal filters are at least one of, (a) digital and (b) analog, filters.

6. A system according to claim 1, including
   a signal reconstruction processor for providing a reconstructed signal by combining the filtered different portions of said signal.

7. A system according to claim 6, wherein
   said signal reconstruction processor provides the reconstructed signal by summing the filtered different portions of said signal.

8. A system according to claim 7, wherein
   said signal reconstruction processor provides said reconstructed signal by performing a weighted summation of the filtered different portions of said signal.

9. A system according to claim 1, wherein
   each of said plurality of adaptive signal filters is associated with a respective filtering characteristic programmable in response to received programming data.

10. A system according to claim 9, wherein
    said programming data is derived in response to data indicating a type of medical procedure being performed.

11. A system according to claim 9, wherein
    the programmable filtering characteristic of said plurality of adaptive signal filters determines whether the filter is at least one of, (a) a low pass filter, (b) a high pass filter and (c) a bandpass filter.

12. A method for adaptively processing patient monitoring signals, comprising:
    acquiring a signal having an amplitude representing electrical activity of a patient heart over time;
    identifying different portions of said signal, where each of the different portions is associated with a different respective phase of cardiac activity, by:
    inverting said signal to provide an inverted signal;
    aligning said signal and said inverted signal based on their respective amplitudes during a cardiac rest portion; and
    identifying one or more of the different portions of said signal based on one or more intersections point of said aligned signal and inverted signal; and
    filtering a respective plurality of bandwidths of each different portion of said signal using a respective adaptive signal filter for each different portion.

13. A method according to claim 12, further comprising:
    generating a reconstructed signal by combining the filtered different portions of said signal.

14. A method according to claim 12, wherein
    each of the adaptive signal filters is associated with a respective filtering characteristic programmable in response to received programming data.

* * * * *